(12) United States Patent
Colli

(10) Patent No.: US 10,213,306 B2
(45) Date of Patent: Feb. 26, 2019

(54) MINIMALLY INVASIVE HEART VALVE REPAIR IN A BEATING HEART

(71) Applicant: NeoChord, Inc., St. Louis Park, MN (US)

(72) Inventor: Andrea Colli, Padua (IT)

(73) Assignee: NeoChord, Inc., St. Louis Park, MN (US)

(*) Notice: Subject to any disclaimer, the term of this patent is extended or adjusted under 35 U.S.C. 154(b) by 19 days.

(21) Appl. No.: 15/662,565

(22) Filed: Jul. 28, 2017

(65) Prior Publication Data

US 2018/0280138 A1  Oct. 4, 2018

Related U.S. Application Data

(60) Provisional application No. 62/479,632, filed on Mar. 31, 2017.

(51) Int. Cl.
| | |
|---|---|
| *A61F 2/24* | (2006.01) |
| *A61B 17/04* | (2006.01) |
| *A61B 17/06* | (2006.01) |
| *A61B 17/00* | (2006.01) |

(52) U.S. Cl.
CPC ........ *A61F 2/2466* (2013.01); *A61B 17/0469* (2013.01); *A61B 17/06004* (2013.01); *A61F 2/2457* (2013.01); *A61B 17/0487* (2013.01); *A61B 2017/00694* (2013.01); *A61B 2017/0496* (2013.01); *A61B 2017/06042* (2013.01)

(58) Field of Classification Search
CPC .. A61F 2/2457; A61F 2/2466; A61B 17/0469; A61B 17/06004; A61B 17/12013
See application file for complete search history.

(56) References Cited

U.S. PATENT DOCUMENTS

| | | |
|---|---|---|
| 5,662,704 A | 9/1997 | Gross |
| 6,506,197 B1 | 1/2003 | Rollero et al. |
| 6,986,775 B2 | 1/2006 | Morales et al. |
| 7,635,386 B1 | 12/2009 | Gammie |
| 7,794,474 B2 | 9/2010 | Michler et al. |
| 7,871,433 B2 | 1/2011 | Lattouf |

(Continued)

FOREIGN PATENT DOCUMENTS

WO   WO 2006/078694 A2   7/2006

OTHER PUBLICATIONS

PCT/US2018/025076, Search Report & Written Opinion dated Jul. 2, 2018, 19 pages.

(Continued)

*Primary Examiner* — Tuan V Nguyen
(74) *Attorney, Agent, or Firm* — Patterson Thuente Pedersen, P.A.

(57) ABSTRACT

In one embodiment, a method of repairing a heart valve accesses an interior of a patient's beating heart minimally invasively and inserts one or more sutures into each of a plurality of heart valve leaflets with a suturing instrument. The suture ends of the sutures are divided into suture pairs, with each pair including one suture end from a suture inserted into a first valve leaflet and one suture end from a suture inserted into a second valve leaflet. One or more tourniquet tubes is advanced over the suture pairs to the leaflets to draw the sutures together to coapt the leaflets and then the sutures are secured in that position.

10 Claims, 18 Drawing Sheets

(56) References Cited

U.S. PATENT DOCUMENTS

| | | | |
|---|---|---|---|
| 8,460,181 B2 | 6/2013 | Saadat et al. |
| 8,465,500 B2 | 6/2013 | Speziali |
| 8,470,028 B2 | 6/2013 | Thornton et al. |
| 8,512,362 B2 | 8/2013 | Ewers et al. |
| 8,523,939 B1 | 9/2013 | Hausen |
| 8,715,302 B2 | 5/2014 | Ibrahim et al. |
| 8,734,505 B2 | 5/2014 | Goldfarb et al. |
| 8,758,393 B2 | 6/2014 | Zentgraf |
| 8,795,295 B2 | 8/2014 | Sauer |
| 8,888,843 B2 | 11/2014 | Khairkhahan et al. |
| 8,938,283 B2 | 1/2015 | Zentgraf et al. |
| 8,968,338 B2 | 3/2015 | Speziali |
| 8,979,750 B2 | 3/2015 | Van Bladel et al. |
| 9,044,221 B2 | 6/2015 | Zentgraf et al. |
| 9,155,622 B2 | 10/2015 | Ruyra Baliarda et al. |
| 9,192,374 B2 | 11/2015 | Zentgraf |
| 9,198,756 B2 | 12/2015 | Aklog et al. |
| 9,364,213 B2 | 6/2016 | Speziali |
| 9,393,080 B2 | 7/2016 | Zentgraf et al. |
| 9,468,364 B2 | 10/2016 | Malchano et al. |
| 9,700,300 B2 | 7/2017 | Speziali |
| 2002/0013571 A1 | 1/2002 | Goldfarb et al. |
| 2004/0044365 A1 | 3/2004 | Bachman |
| 2004/0097979 A1 | 5/2004 | Svanidze et al. |
| 2004/0181238 A1 | 9/2004 | Zarbatany et al. |
| 2005/0075727 A1* | 4/2005 | Wheatley ............ A61F 2/2412 623/2.17 |
| 2005/0216039 A1 | 9/2005 | Lederman |
| 2007/0049952 A1* | 3/2007 | Weiss ............ A61B 17/0218 606/144 |
| 2007/0093857 A1 | 4/2007 | Rogers et al. |
| 2007/0112425 A1 | 5/2007 | Schaller et al. |
| 2008/0188873 A1 | 8/2008 | Speziali |
| 2008/0195126 A1 | 8/2008 | Solem |
| 2008/0228223 A1 | 9/2008 | Alkhatib |
| 2009/0105729 A1 | 4/2009 | Zentgraf |
| 2009/0105751 A1 | 4/2009 | Zentgraf |
| 2009/0306685 A1 | 12/2009 | Fill |
| 2010/0174297 A1 | 7/2010 | Speziali |
| 2010/0331971 A1 | 12/2010 | Keranen et al. |
| 2012/0184971 A1 | 7/2012 | Zentgraf et al. |
| 2013/0035757 A1 | 2/2013 | Zentgraf et al. |
| 2013/0072786 A1 | 3/2013 | Keogh et al. |
| 2013/0150710 A1 | 6/2013 | Zentgraf et al. |
| 2013/0231533 A1 | 9/2013 | Papademtriou et al. |
| 2014/0018912 A1 | 1/2014 | Delaloye et al. |
| 2014/0039324 A1 | 2/2014 | Speziali |
| 2014/0148825 A1 | 5/2014 | Nobles et al. |
| 2014/0276979 A1 | 9/2014 | Sauer et al. |
| 2014/0364875 A1 | 12/2014 | Zentgraf |
| 2015/0018879 A1 | 1/2015 | Moehle et al. |
| 2015/0134057 A1 | 5/2015 | Rourke et al. |
| 2015/0148821 A1 | 5/2015 | Speziali |
| 2015/0190207 A1 | 7/2015 | Zentgraf et al. |
| 2015/0313713 A1 | 11/2015 | Zentgraf et al. |
| 2016/0143737 A1 | 5/2016 | Zentgraf et al. |
| 2017/0049435 A1* | 2/2017 | Sauer ............ A61B 17/0401 |
| 2017/0290582 A1 | 10/2017 | Speziali |

OTHER PUBLICATIONS

Cilingiroglu et al., "Percutaneous Mitral Valve Repair with MitraClip," Turk Kardiyoloji Dernegi arsivi, dated Mar. 2012, 2 pages.

Naqvi et al., "Beating-Heart Percutaneous Mitral Valve Repair Using a Transcatheter Endovascular Suturing Device in an Animal Model," Official Journal of the Society for Cardiac Angiography & Interventions, Mar. 2, 2007, 3 pages.

Mitralign, "Mitral Regurgitatic, Functional Mitrial Regurgitation," dated Dec. 6, 2016, 3 pages.

* cited by examiner

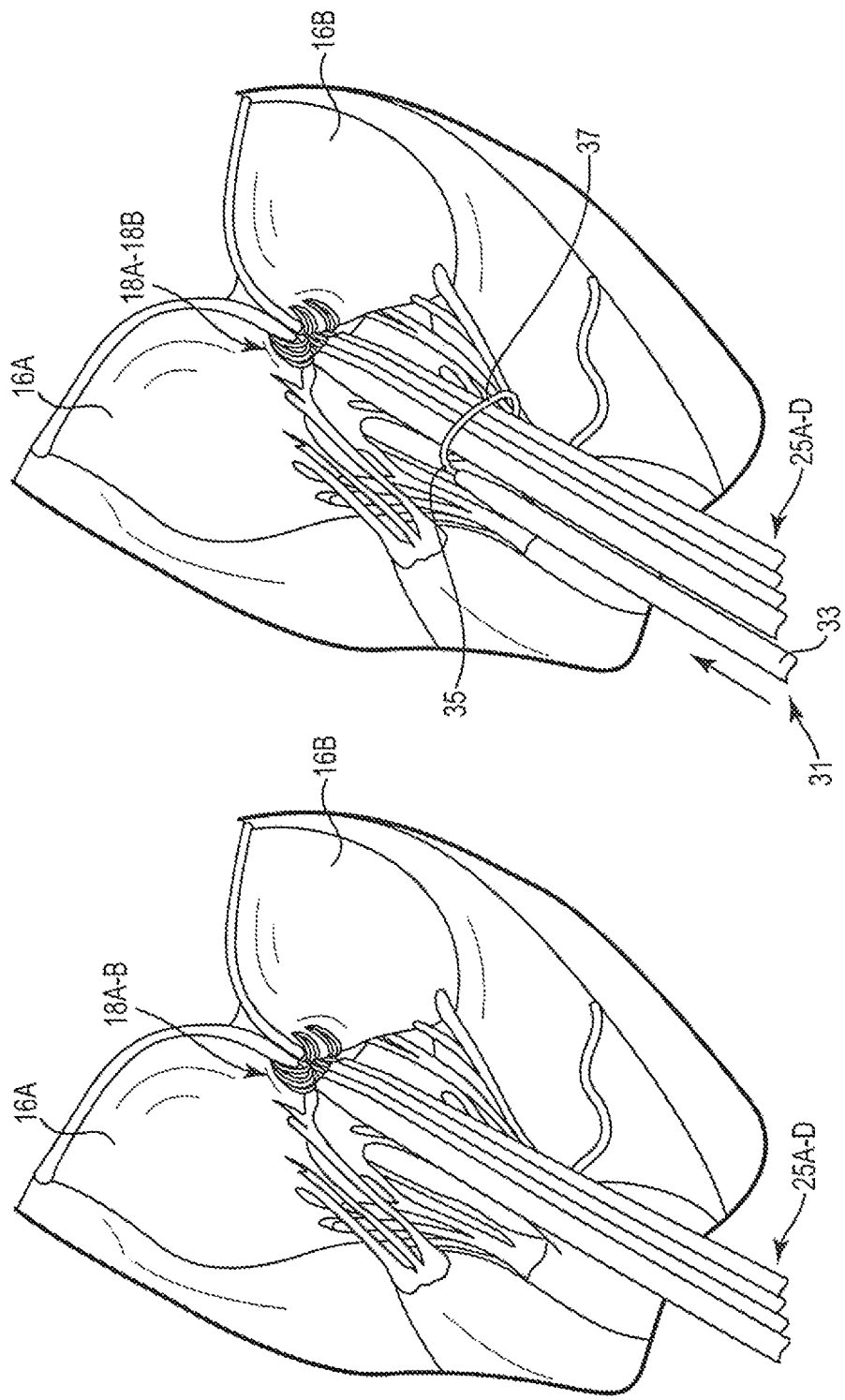

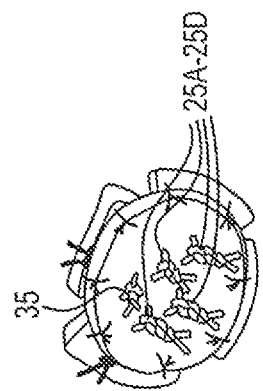
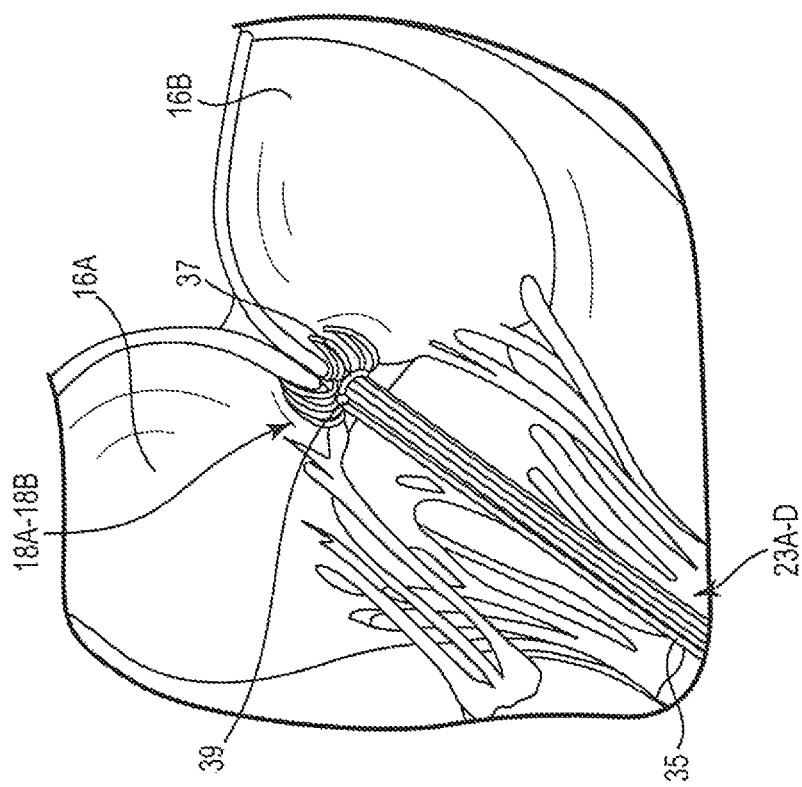

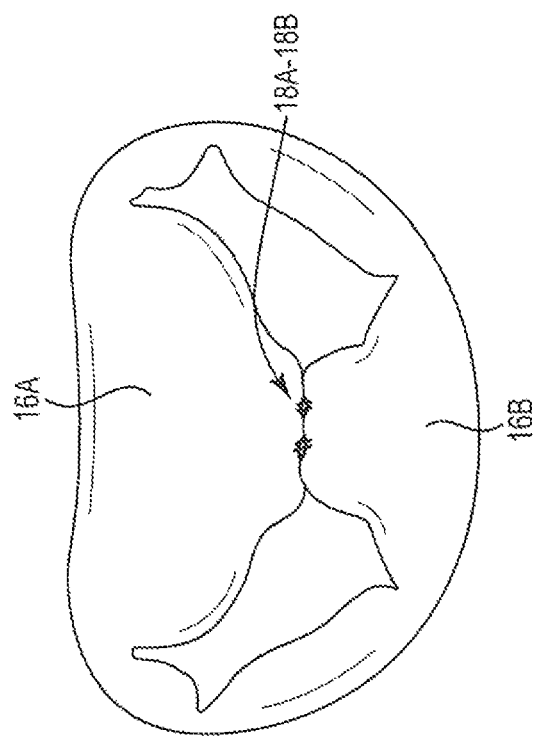

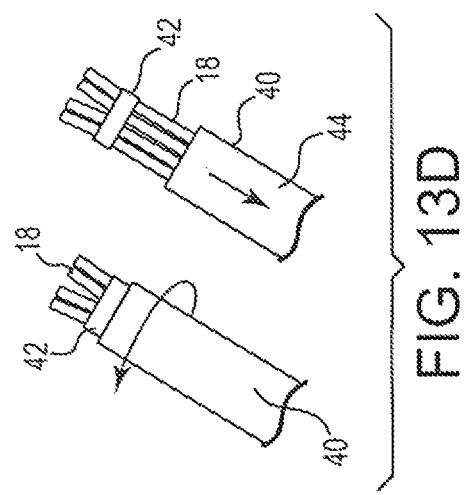
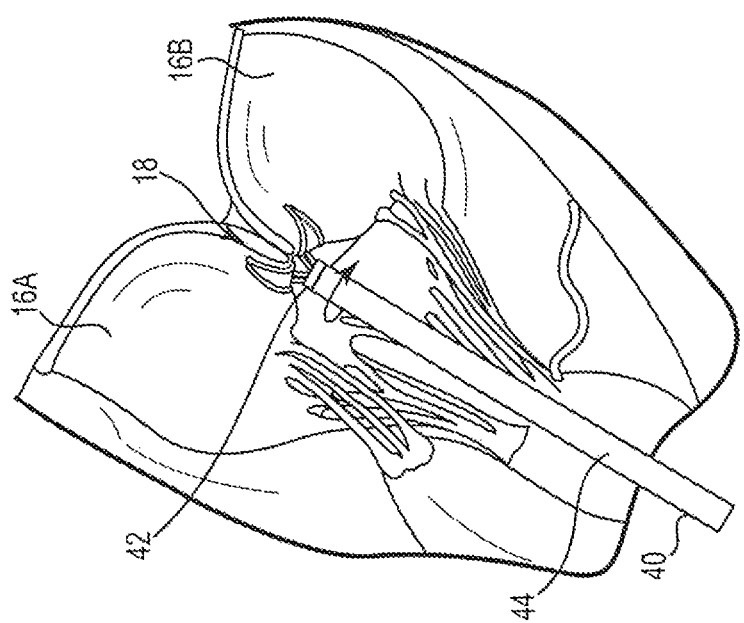
FIG. 13C
FIG. 13D

MINIMALLY INVASIVE HEART VALVE REPAIR IN A BEATING HEART

RELATED APPLICATION

This application claims the benefit of U.S. Provisional Application No. 62/479,632 filed Mar. 31, 2017, which is hereby fully incorporated herein by reference.

TECHNICAL FIELD

The present disclosure relates to minimally invasive repair of a heart valve while the patient's heart is beating. More particularly, embodiments of the present invention relate to minimally invasive systems and methods for performing an edge to edge heart valve leaflet repair on a beating heart.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart by a thoracotomy generally requires isolation of the heart and coronary blood vessels from the remainder of the arterial system, and arrest of cardiac function (an "open heart" procedure). Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest are intracardiac procedures for surgical treatment of heart valves, especially the mitral and aortic valves. Tens of thousands of patients are diagnosed with aortic and mitral valve disease each year. Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts. Valve replacement, however, can present a number of difficulties including that the invasiveness of the procedure can lead to long recovery times and that the irregular shape of the valve annulus can cause difficulty in properly fixing and orienting the replacement valve, which can lead to leaks and other problems. Therefore, in situations where patients can adequately be treating by repairing, rather than replacing, the valve, it is generally preferable to do so.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This typically open heart operation is generally carried out through a median sternotomy and requires cardiopulmonary bypass with aortic cross-clamp and cardioplegic arrest of the heart, as described above.

Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

Techniques have been developed and are under development for minimally invasive thorascopic repair of heart valves while the heart is still beating. Int'l Pub. No. WO 2006/078694 A2 to Speziali discloses a thorascopic heart valve repair method and apparatus. Instead of requiring open heart surgery on a stopped heart, the thorascopic heart valve repair methods and apparatus taught by Speziali utilize fiber optic technology in conjunction with transesophageal echocardiography (TEE) as a visualization technique during a minimally invasive surgical procedure that can be utilized on a beating heart. U.S. Publication No. 2008/0228223 to Alkhatib also discloses an apparatus for attaching a prosthetic tether between a leaflet of a patient's heart valve and another portion of the patient's heart to help prevent prolapse of the leaflet and/or to otherwise improve leaflet function.

More recent versions of these techniques are disclosed in U.S. Patent Application Publication Nos. 2009/0105751 and 2009/0105729 to Zentgraf, which disclose an integrated device that can enter the heart chamber, navigate to the leaflet, capture the leaflet, confirm proper capture, and deliver a suture as part of a mitral valve regurgitation (MR) repair. These references are hereby incorporated by reference herein in their entirety.

An alternative to the above-described techniques that insert a suture through a single valve leaflet and anchor the suture to the heart is an edge to edge valve repair. In a traditional Alfieri edge to edge procedure, the edges of adjacent valve leaflets are sutured together to coapt the leaflets using an open surgical approach. This technique has been mimicked in minimally invasive, beating heart procedures by employing a clip that joins the leaflets together rather than a suture. U.S. Patent Publication No. 2004/0044365 to Bachman discloses a technique for minimally invasively accessing the heart through an endovascular approach to perform and edge to edge repair. After sutures are inserted into the leaflets, the sutures can be knotted external to the patient's body and advanced to the repair site with a knot-pushing device as shown, for example, in U.S. Pat. Nos. 8,202,282 and 8,075,574. However, it has been found that it can be difficult to stabilize the leaflets to maintain appropriate tension when knotting sutures in such a fashion and that it can be difficult for the knot pusher to properly advance the knot all the way to the leaflets. In addition, use of such a knot pusher risks damage to other structures within the heart. There is therefore a need for a technique for performing an edge to edge repair on a beating heart of a patient that secures the leaflets together at a proper tension in a more effective manner.

SUMMARY OF THE INVENTION

Disclosed herein are minimally invasive systems and methods for performing an edge to edge repair of a heart valve on a beating heart of a patient. One or more sutures are inserted into a plurality of leaflets of the heart valve while the heart is beating through a minimally invasive access. The sutures are secured at an appropriate tension to maintain the leaflets in a coapted position.

In one embodiment, a method of repairing a heart valve accesses an interior of a patient's beating heart minimally invasively and inserts one or more sutures into each of a plurality of heart valve leaflets with a suturing instrument. The suture ends of the sutures are divided into suture pairs, with each pair including one suture end from a suture inserted into a first valve leaflet and one suture end from a suture inserted into a second valve leaflet. One or more tourniquet tubes is advanced over the suture pairs to the leaflets to draw the sutures together to coapt the leaflets and then the sutures are secured in that position.

In one embodiment, the sutures are secured with a suture loop of a ligature assembly. The suture loop is advanced to the leaflets along the tourniquet tube(s) and tightened around the sutures to secure the position and the tourniquet tube(s) withdrawn. The sutures and ligature suture are then tied off to maintain the leaflets in an edge to edge, coapted configuration.

In another embodiment, the sutures are secured with a stabilizing tourniquet tube having a clip or suture loop positioned at its distal end. The stabilizing tourniquet tube is advanced over the sutures as described above and the sutures are secured by disconnecting a body portion of the tourniquet tube from the clip or sutures after causing the clip or sutures to be cinched around the sutures.

A system for minimally invasively repairing a heart valve in a beating heart of a patient includes a suturing instrument, a plurality of sutures, one or more tourniquet tubes, and a means for securing the sutures under tension with the leaflets in a coapted position. The suturing instrument is used to insert a plurality of sutures into the valve leaflets of the valve while the heart is beating. The one or more tourniquet tubes are used to draw the sutures together to coapt the leaflets and maintain the sutures in position so that they can be secured in that position. In various embodiments, the sutures can be secured in position with, for example, a ligature assembly, or a clip deployed by a tourniquet tube.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

BRIEF DESCRIPTION OF THE DRAWINGS

The invention may be more completely understood in consideration of the following detailed description of various embodiments of the invention in connection with the accompanying drawings, in which:

FIGS. 9A-9I schematically depict a method of performing an edge to edge repair of a heart valve with sutures on a beating heart of a patient according to an embodiment of the present invention;

FIGS. 13A-13D schematically depict a portion of a method of performing an edge to edge repair of a heart valve with sutures on a beating heart of a patient according to an embodiment of the present invention;

Figure 1:
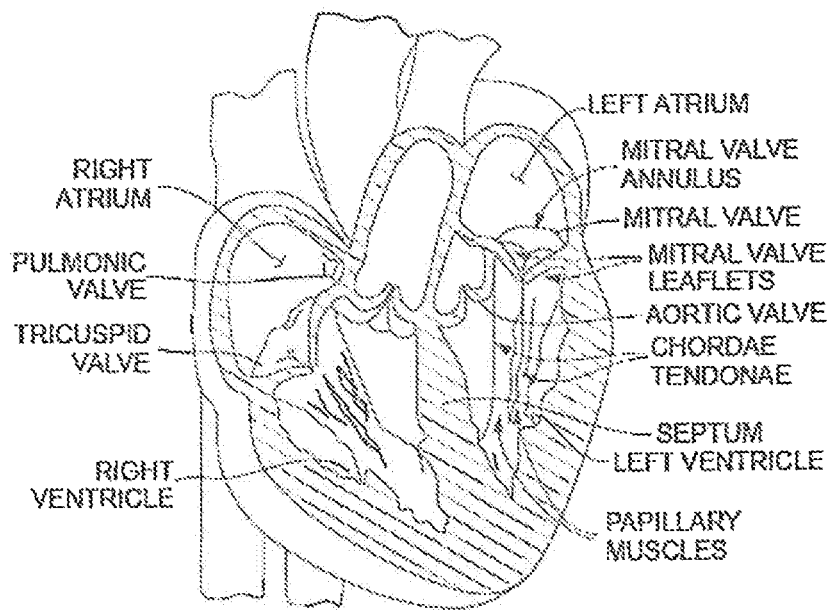
FIG. 1 is a schematic cross-sectional view of a heart.
Figure 2:
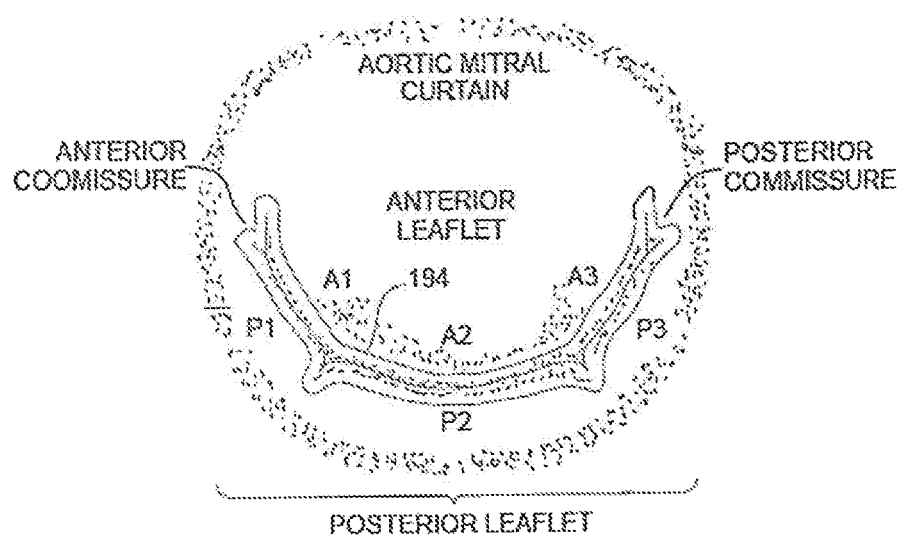
FIG. 2 is a schematic top plan view of a mitral valve.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications equivalents, and alternatives falling within the spirit and scope of the invention.

DETAILED DESCRIPTION

A mitral valve is schematically depicted in FIGS. 1-3B. Situated between the left atrium and left ventricle, the mitral valve consists of two flaps of tissue, or leaflets (a posterior leaflet and an anterior leaflet). The mitral valve annulus forms a ring around the valve leaflets, thereby connecting the leaflets to the heart muscle. Papillary muscles are located at the base of the left ventricle. Tendon-like cords called chordae tendineae anchor the mitral valve leaflets to the papillary muscles. Normal chordae tendineae prevent the leaflets from prolapsing, or inverting, into the left atrium, as depicted in FIG. 3A.

Under normal cardiac conditions, the left atrium contracts and forces blood through the mitral valve and into the left ventricle. As the left ventricle contracts, hemodynamic pressure forces the mitral valve shut and blood is pumped through the aortic valve into the aorta. For the mitral valve to shut properly, the valvular edges of the valve leaflets must form a non-prolapsing seal, or coaptation, that prevents the backflow of blood during left ventricular contraction.

Figure 3A:
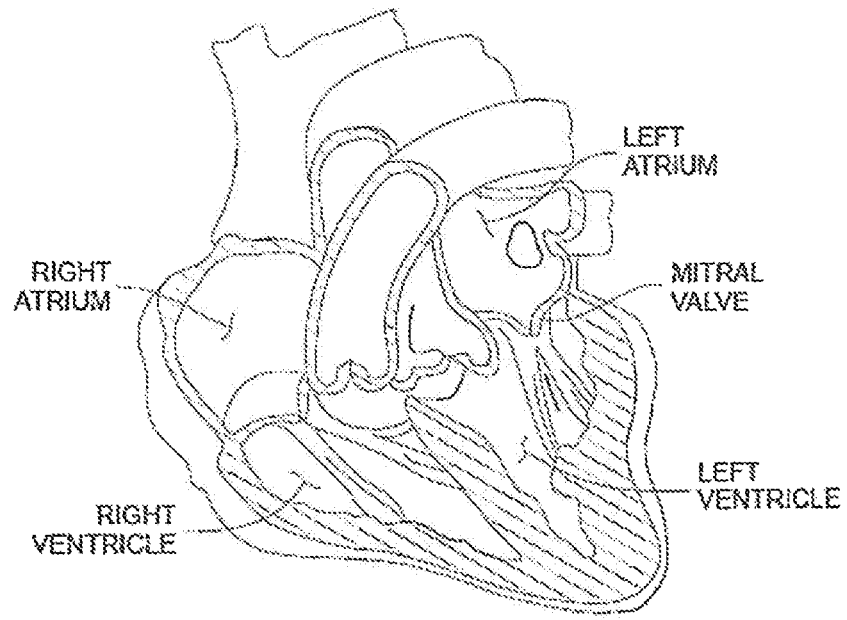
FIG. 3A is a schematic cross-sectional view of a heart with a normal mitral valve.
Figure 3B:
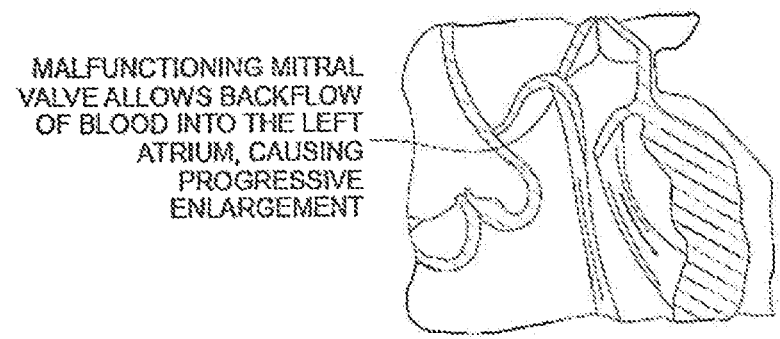
FIG. 3B is a partial schematic cross-sectional view of a heart with an abnormal mitral valve.

A properly functioning mitral valve opens and closes fully. When the mitral valve fails to fully close, as depicted in FIG. 3B, blood from the left ventricle is able to flow backward into the left atrium instead of flowing forward into the aorta. This backflow of blood through the heart valve is called regurgitation. The regurgitation of blood through the heart due to the failure of the mitral valve to close properly (coapt) is the condition known as mitral valve regurgitation (MR). A common symptom of mitral valve regurgitation is congestion of blood within the lungs.

When blood regurgitates from the left ventricle into the left atrium, such as due to MR, less blood is pumped into the aorta and throughout the body. In an attempt to pump adequate blood to meet the blood needs of the body, the left ventricle tends to increase in size over time to compensate for this reduced blood flow. Ventricular enlargement, in turn, often leads to compromised contractions of the heart, thereby exacerbating the congestion of blood within the lungs. If left untreated, severe MR can eventually lead to serious cardiac arrhythmia and/or congestive heart failure (CHF).

Mitral valve regurgitation can be caused by any number of conditions, including mitral valve prolapse (a condition in which the leaflets and chordae tendineae of the mitral valve are weakened resulting in prolapse of the valve leaflets, improper closure of the mitral valve, and the backflow of blood within the heart with each contraction of the left ventricle), damaged chords (wherein the chordae tendineae become stretched or ruptured, causing substantial leakage through the mitral valve), ventricular enlargement, rheumatic fever (the infection can cause the valve leaflets to thicken, limiting the valve's ability to open, or cause scarring of the leaflets, leading to regurgitation), endocarditis (an infection inside the heart), deterioration of the mitral valve with age, prior heart attack (causing damage to the area of the heart muscle that supports the mitral valve), and a variety of congenital heart defects. As MR becomes exacerbated over time, the condition can become more severe, resulting in life-threatening complications, including atrial fibrillation (an irregular heart rhythm in which the atria beat chaotically and rapidly, causing blood clots to develop and break loose and potentially result in a stroke), heart arrhythmias, and congestive heart failure (occurring when the heart becomes unable to pump sufficient blood to meet the body's needs due to the strain on the right side of the heart caused by fluid and pressure build-up in the lungs).

The present application describes various devices and methods that can be employed on the beating heart of a patient in a minimally invasive manner to treat mitral valve regurgitation as described above. Embodiments as described herein can be used to restrain a prolapsing leaflet to prevent leaflet prolapse and to promote leaflet coaptation. According to certain embodiments, the present invention generally reduces the need to perform an edge to edge valve repair with a suture with a sternotomy and cardiopulmonary bypass surgery. Specifically, the present invention can provide a minimally invasive edge to edge treatment of MR. This treatment significantly decreases trauma to surgical patients by facilitating transapical access of a beating heart via a lateral thoracotomy in a manner that eliminates certain surgical steps normally required to complete mitral valve repair procedure by sternotomy.

In certain embodiments, the methods described herein are performed via transapical access. Transapical access to a heart includes all entry points that are within approximately the bottom third of the heart. As used in this patent application, transapical access to a heart includes all directions of entry and points of entry, as well as all angles of entry at each entry point. Further details regarding such access can be found in PCT Publication No. WO 2006/078694 to Speziali, which is hereby incorporated herein by reference in its entirety. In other embodiments, the methods can be performed via an endovascular approach, such as a transfemoral, transseptal approach. Further details regarding such an endovascular access approach can be found in U.S. Patent Publication No. 2016/014737, which is hereby incorporated by reference in its entirety.

Figure 4:
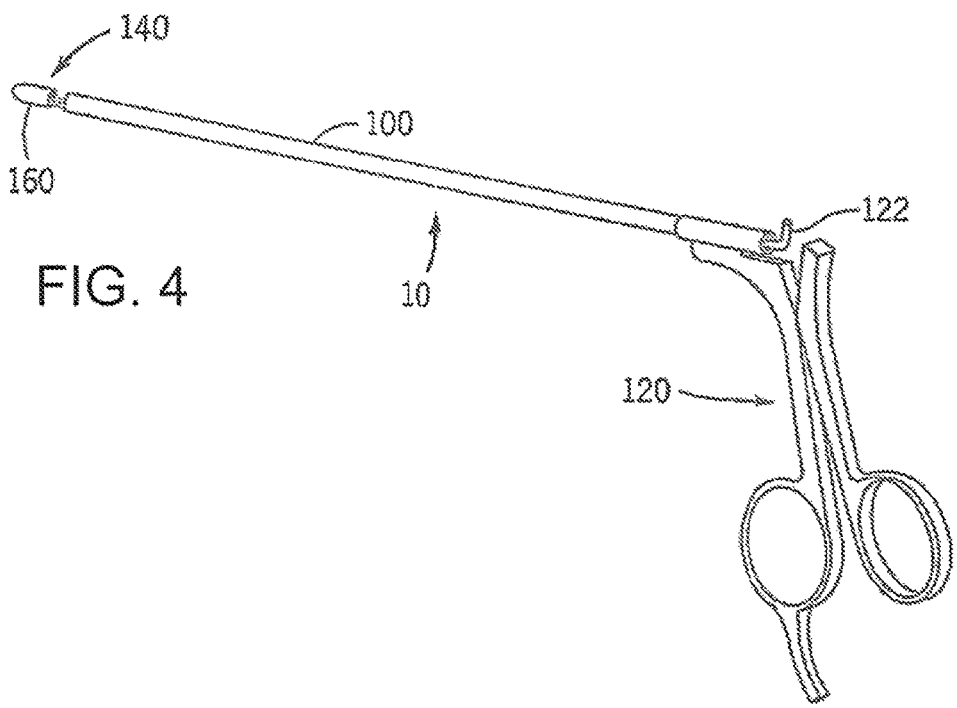
FIG. 4 is an isometric view of an instrument the can be employed with embodiments of the present invention.
Figure 5:
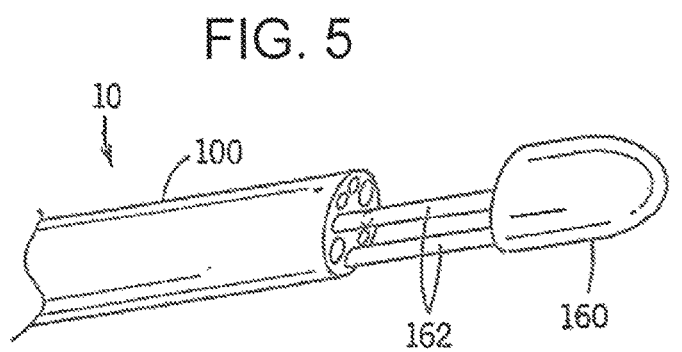
FIG. 5 is a detailed isometric view of the distal end of the instrument of FIG. 4.

One embodiment of an instrument 10 that can be used in performing the methods described herein is depicted in FIGS. 4 and 5. Instrument 10 includes a rigid metal shaft 100 having a handle 120 at its extrathoracic (proximal) end that enables the instrument to be manipulated and guided into position. Actuating mechanisms for controlling the grasping mechanism and needle mechanism located at the distal end 140 of the instrument are also mounted near the handle 120. The grasping mechanism is operated by squeezing the scissor-grip handle 120, and the needle mechanism is operated by moving an up-turned control shaft 122.

Figure 6A:
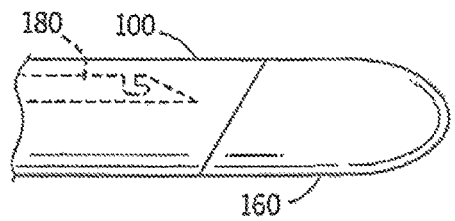
FIG. 6A is a detailed side elevation view of the distal end of the instrument of FIG. 4 showing the tip in a closed position.
Figure 6B:
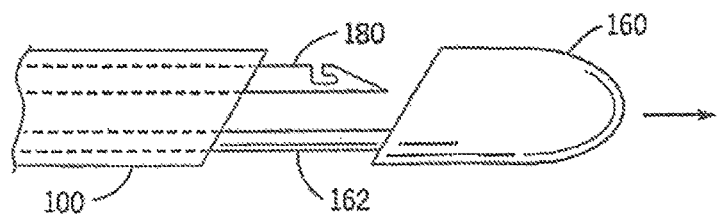
FIG. 6B is a detailed side elevation view of the distal end of the instrument of FIG. 4 showing rods inside the instrument that are capable of sliding to move the tip to an open position.
Figure 7:
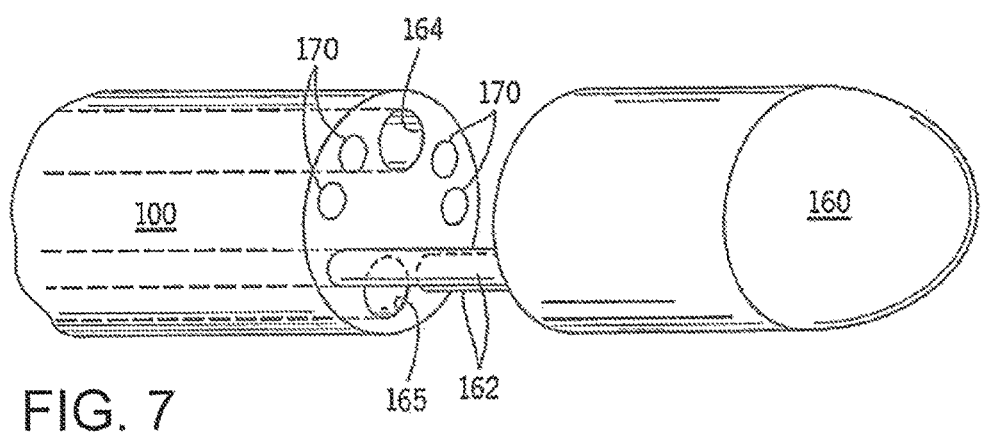
FIG. 7 is a detailed isometric view of the distal end of the instrument of FIG. 4 showing the needle lumen and four fiberoptic channels that are disposed around the needle lumen.

Located on the distal, intracardiac end 140 of the instrument 10 is a grasping mechanism which can be operated to hold a valve leaflet. As shown in FIGS. 5, 6A, 6B, and 7, in one embodiment this mechanism is a tip 160 which is supported on the distal end of the shaft 100 by a set of rods 162. The rods 162 slide within the shaft 100 to move the tip 160 between an open position as shown in FIGS. 6B and 7 and a closed position as shown in FIG. 6A when the scissor-grip handle 120 is operated. As will be explained below, a valve leaflet is located in the gap between the open tip 160 and the distal end of shaft 100 and it is captured by closing the tip 160 to pinch the valve leaflet therebetween.

Disposed in a needle lumen 164 formed in the shaft 100 is a needle 180 which connects to the control shaft 122 at the proximal end of shaft 100. Needle mechanism 180 slides between a retracted position in which it is housed in the lumen 164 near the distal end of the shaft 100 and an extended position in which it extends into the sliding tip 160 when the tip is in its closed position. As a result, if a valve leaflet has been captured between the tip 160 and the distal end of shaft 100 the needle may be extended from the lumen 164 by moving control shaft 122 to puncture the captured leaflet and pass completely through it.

The distal end of the shaft 100 can also contain an artificial chorda, or suture 18 that is to be deployed in the patient's heart. The suture 18 is typically a 4-0 or 5-0 suture manufactured by a company such as Gore-Tex. This suture 18 is deployed by the operation of the grasping mechanism and the needle mechanism 180 as described in more detail below.

The shaft 100 has a size and shape suitable to be inserted into the patient's chest and through the left ventricle cardiac wall and form a water-tight seal with the heart muscle. It has a circular or ellipsoidal cross-section and it houses the control links between the handle end and the intracardiac end of the instrument as well as a fiber optic visualization system. Further details regarding example embodiments of such devices can be found in U.S. Pat. Nos. 8,465,500; 8,758,393; and 9,192,374, each of which is hereby incorporated by reference herein in its entirety.

Figure 8A:
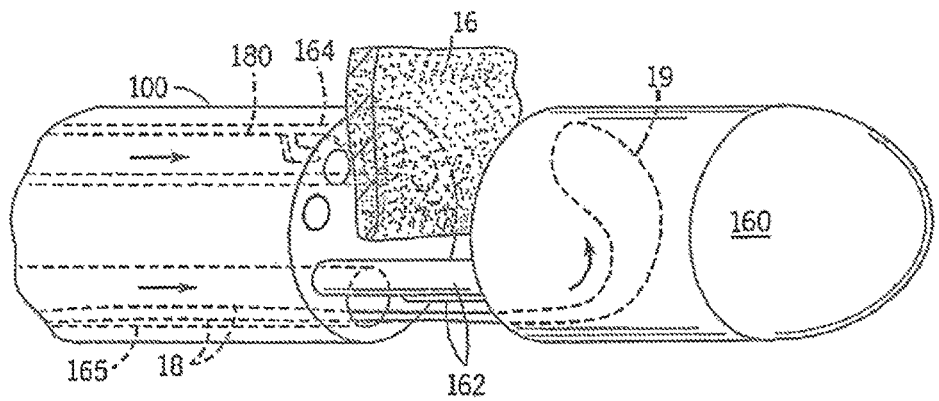
FIGS. 8A-8F depict detailed isometric view of a suture being deployed into a heart valve leaflet according to embodiments of the present invention.
Figure 8B:
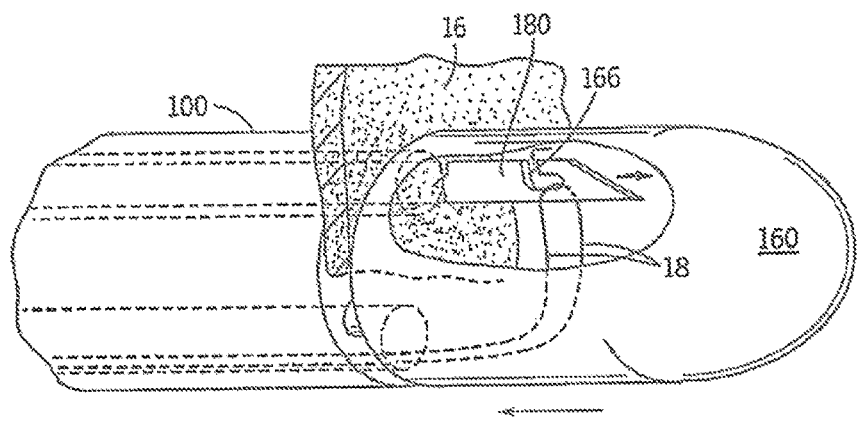
Figure 8C:
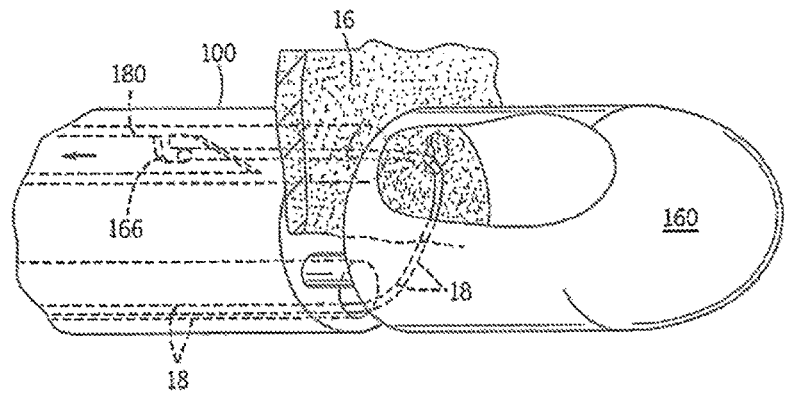
Figure 8D:
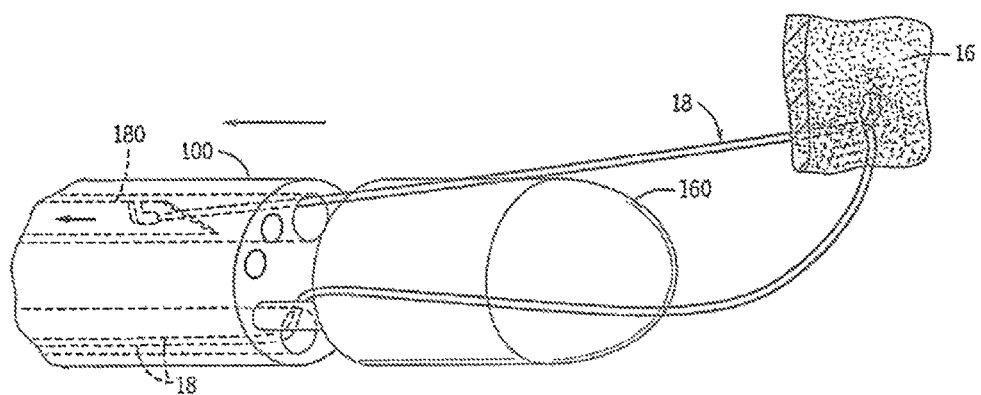
Figure 8E:
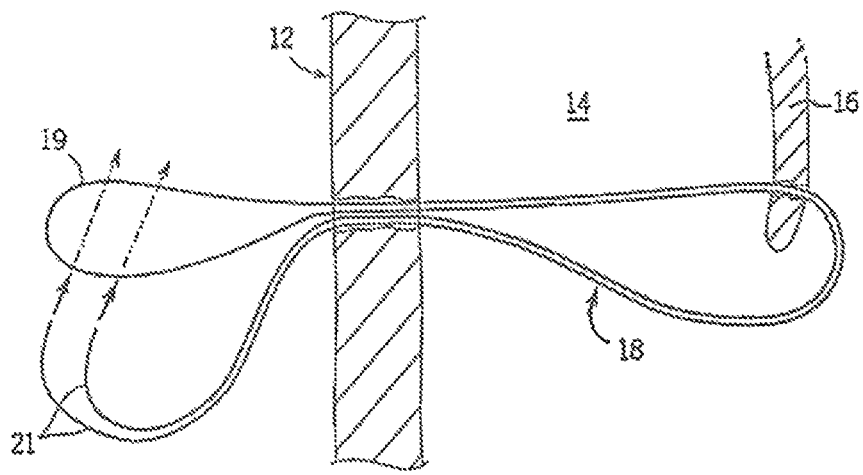
Figure 8F:
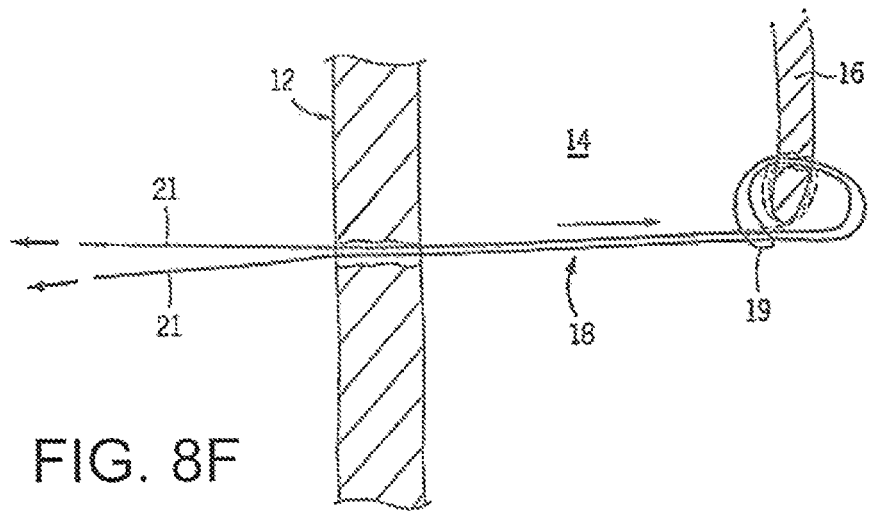

As shown in FIGS. 8A-8F, a suture can be deployed into a heart valve leaflet of a beating heat of a patient with instrument 10 and other similar instruments described herein. Instrument 10 is positioned around a valve leaflet 16 to be repaired as shown in FIG. 8A. In one embodiment, the suture 18 can be folded at the middle to form a loop 19 that is positioned in the tip 160. Both ends of the suture 18 can be disposed in a suture lumen 165 formed in the shaft 100 beneath the rods 162. As shown in FIG. 8B, the valve leaflet 16 is grasped by closing the tip 160, and the needle 180 is extended to puncture the leaflet 16 and extend into the tip 160. A notch 166 formed on one side of the needle 180 hooks the suture loop 19. The needle 180 is then retracted back through the leaflet 16 to pull the suture loop 19 through the puncture opening as shown in FIG. 8C. The leaflet 16 is then released and the instrument 10 is withdrawn from the heart as shown in FIG. 8D pulling both ends and the midpoint of the suture 18 with it. As shown in FIG. 8E, the suture 18 is released by the instrument 10 and the surgeon inserts the two suture ends 21 through the loop 19 at its midpoint. The ends 21 are then pulled and the loop 19 slides along the suture 18 back into the heart chamber 14 where it forms a Larks head around the edge of the valve leaflet as shown in FIG. 8F. At this point, the two free ends 21 of the suture 18 are external to the heart wall at the apex 12 of the heart. Multiple sutures 18 may be implanted in this manner.

Figure 9B:
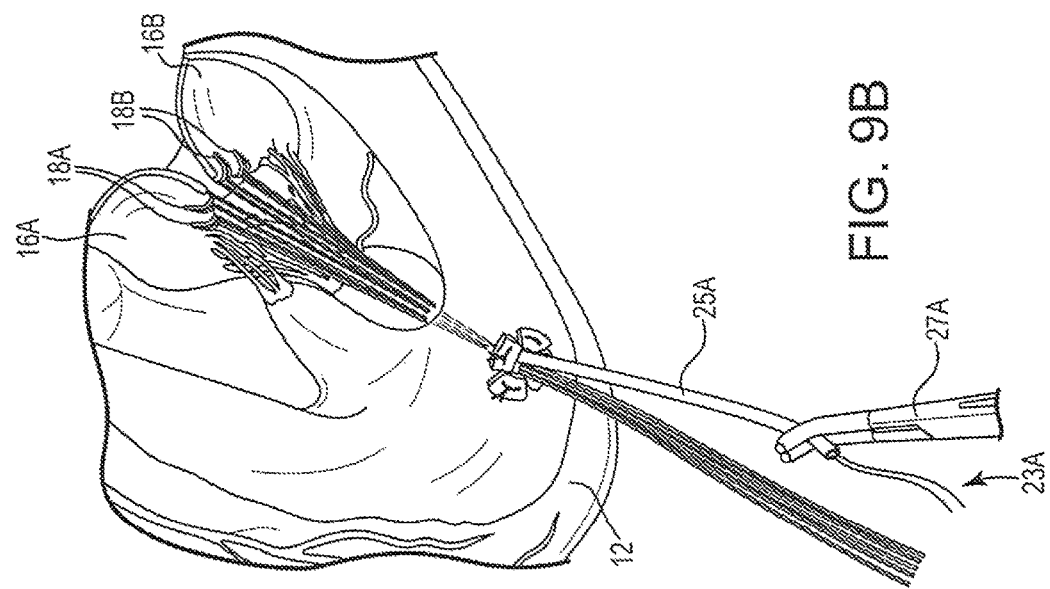
Figure 9A:
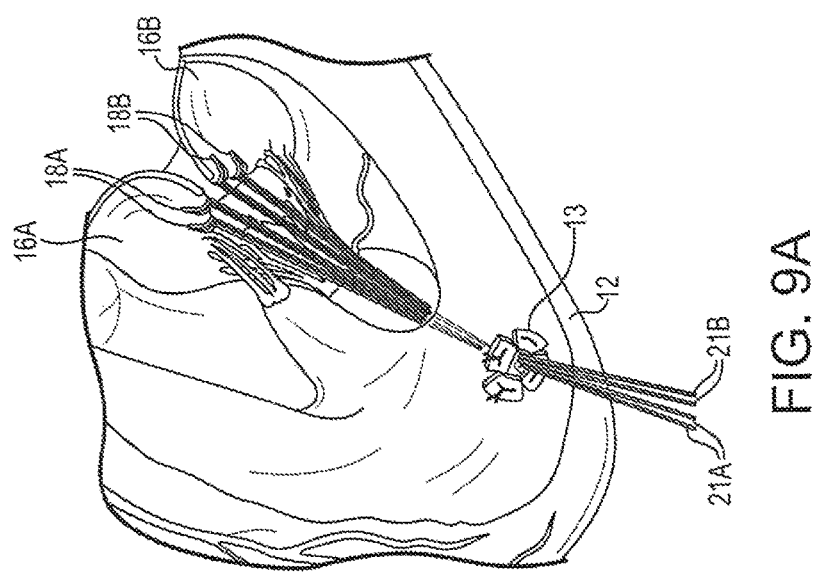
Figure 9D:
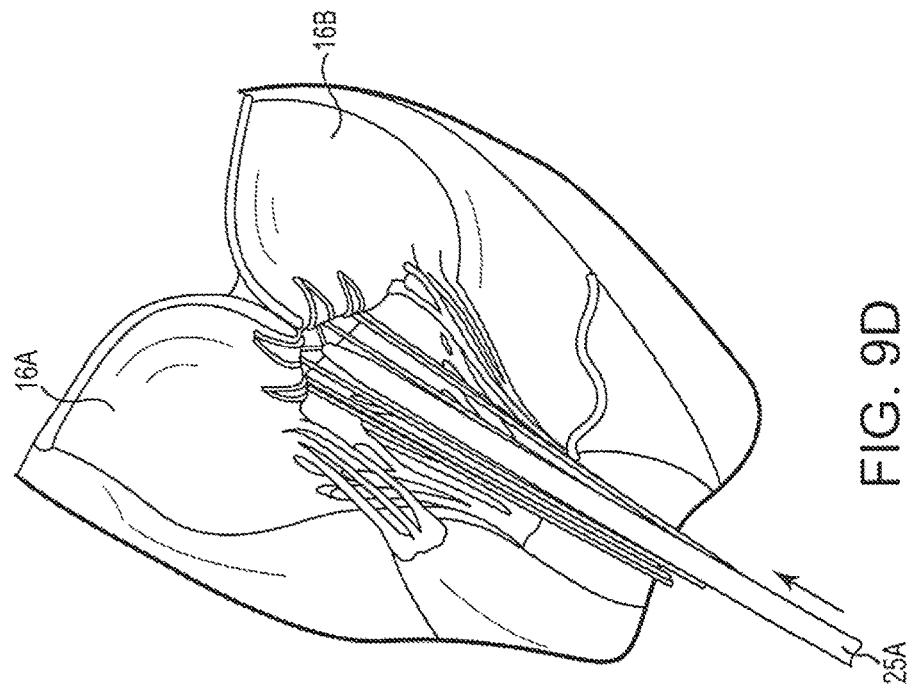
Figure 9C:
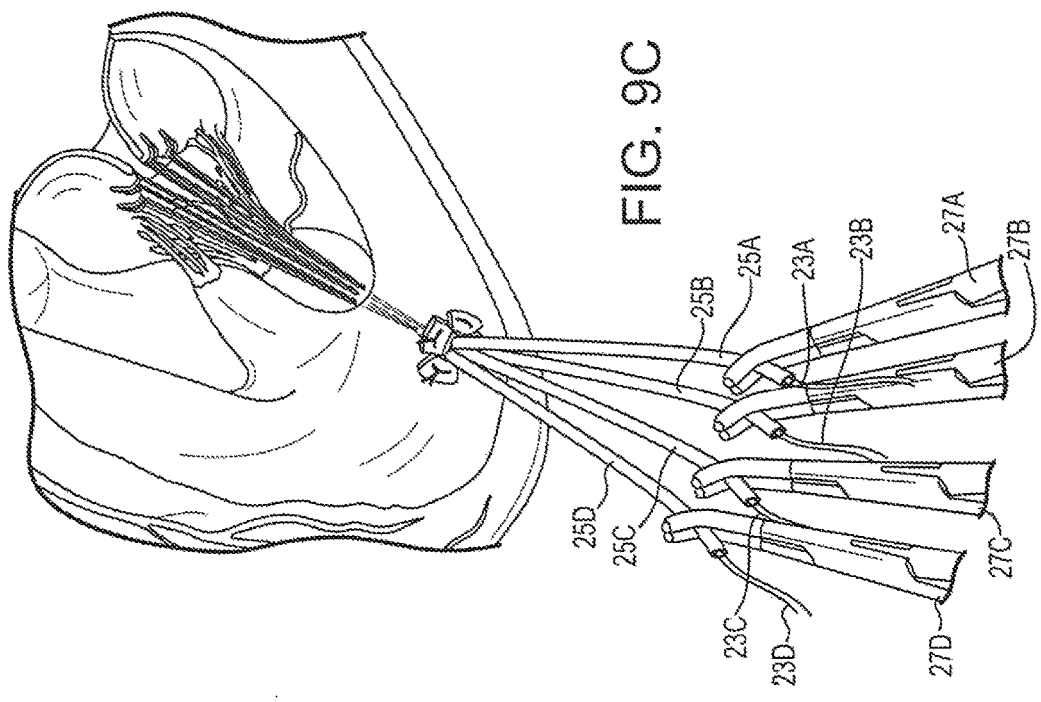

FIGS. 9A-9I schematically depict a method of performing an edge to edge repair of a heart valve with sutures on a beating heart of a patient according to an embodiment of the present invention. Referring to FIG. 9A, in this embodiment access to the heart has been gained through the apical region 12 of the heart and a purse-string suture 13 has been placed at the access location. A plurality of sutures 18 have already been inserted into the valve leaflets using, for example, instruments and methods as described above. In the depicted embodiment, two sutures 18A have been inserted into a first leaflet 16A and two sutures 18B have been inserted into a second leaflet 16B. With respect to the mitral valve, one of the first and second valve leaflets 16A, 16B is the anterior leaflet and the other is the posterior leaflet. As described above, each suture 18A-18B forms a loop around the respective leaflet with a respective pair of free ends 21A-21B extending out of the heart. In other embodiments, different numbers of sutures could be used. For example, in one embodiment, one suture is inserted through each leaflet. Referring to FIGS. 9B and 9C, the suture ends 21A, 21B are divided into a plurality of suture pairs 23. Each suture pair 23A-23D consists of one suture end 21A extending from the first leaflet 16A and one suture end 21B extending from the second leaflet 16B, such that each suture pair is connected to both leaflets. As can be seen in FIG. 9B, the sutures in the first suture pair 23A are threaded through a tourniquet tube 25A (e.g., a small, thin tube of plastic or similar material) and stabilized with, for example, a mosquito forceps 27A. Each of the other suture pairs 23B-23D is also threaded through a corresponding tourniquet tube 25B-25D and secured with a forceps 27B-27D. In one embodiment, each corresponding tourniquet tube and forceps, e.g., tourniquet tube 25A and forceps 27A are a common color with each other corresponding pair being a different color to enable the surgeon to easily differentiate among the pairs and to prevent potential crossing of the sutures.

Referring now to FIG. 9D, the first tourniquet tube 25A is advanced along the suture pair 23A and introduced into the heart after disengaging the mosquito forceps 27A. The tourniquet tube 25A is advanced until it reaches the leaflets. This pulls the suture ends in the suture pair 23A closer together increasing the tension thereon and drawing the leaflets 16A-16B closer together, i.e., generally into an edge to edge configuration. The mosquito forceps 27A can then again be clamped onto the tourniquet tube 25A in order to retain the relative position of the tourniquet tube 25A and suture pair 23A and the tension of the sutures to maintain the leaflets in coaptation. The same procedure is conducted with tourniquet tubes 25B-25D and suture pairs 23B-23D as shown in FIG. 9E. This draws the leaflets 16A, 16B towards coaptation at four distinct locations, corresponding to each of the suture pairs 23A-23D. At this stage, the efficacy of the procedure can be assessed using real-time transesophageal echocardiography to confirm proper valve function.

As can be seen in FIGS. 9F and 9G, a ligature assembly 31 can be used to secure the sutures 18A-18D at the required tension for coaptation of the leaflets 16A, 16B as temporarily stabilized through use of the tourniquet tubes 25A-25D and forceps 27A-27D. The ligature assembly 31 includes a tube 33 containing a suture 35 that presents a knot 39 forming a ligature loop 37 at its distal end. In one embodiment, ligature assembly is an Endoloop® PDS Ligature, available from Ethicon US, LLC. As shown in FIG. 9F, the loop 37 is positioned around all of the tourniquet tubes 25A-25D and advanced therealong towards the leaflets 16A, 16B with the plastic tube 33. Once the loop 37 has reached the leaflets 16A, 16B, it is tightened around the sutures 18A-18D via the knot 39 as shown in FIG. 9G to maintain the suture pairs 23A-23D under tension to retain the leaflets 16A, 16B in coaptation. Use of tourniquet tubes 25A-25D not only provides a more effective means for maintaining the sutures under an appropriate tension, it further protects subvalvular and other internal heart structures from damage by guiding the ligature assembly towards the leaflets and constraining the range and direction of motion the assembly can have within the heart.

The tourniquet tubes 25A-25D are then withdrawn from the sutures 18A-18D and each of the suture pairs 23A-23D and the ligature suture 35 are tied off at the access point 13 at the apex 12 of the heart as shown in FIG. 9H. The leaflets 16A, 16B are retained in an edge to edge, coapted position by the sutures 18A-18D as shown in FIG. 9I. By tying off the sutures at the apex to the heart, the sutures are aligned similarly to chordae tendinaea, and therefore provide a more natural coaptation point for the leaflet as compared to simply suturing or clipping the leaflets together.

Figure 10B:
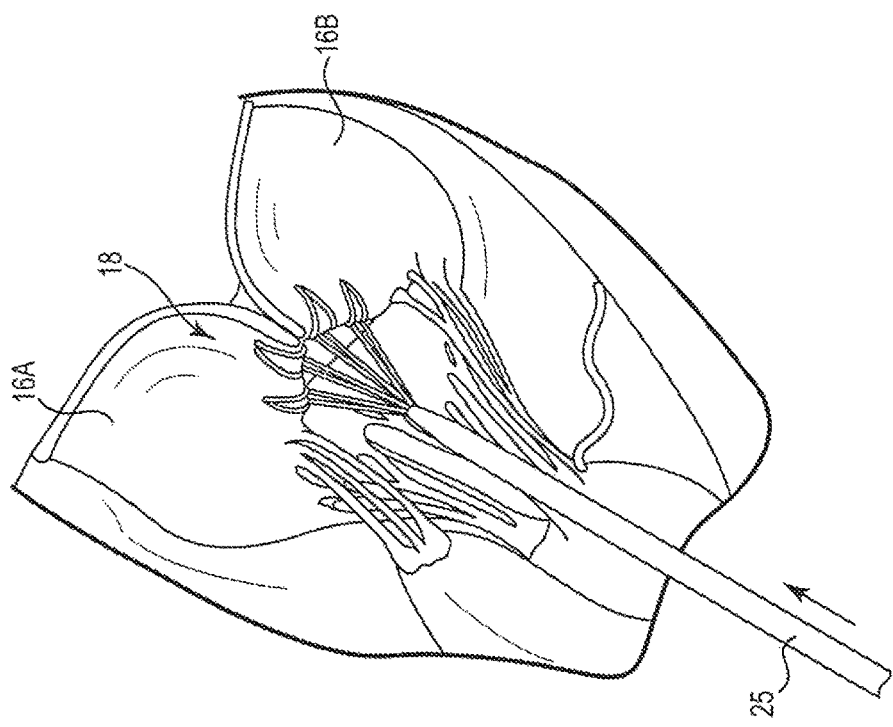
FIGS. 10A-10D schematically depict a portion of a method of performing an edge to edge repair of a heart valve with sutures on a beating heart of a patient according to an embodiment of the present invention.
Figure 10A:
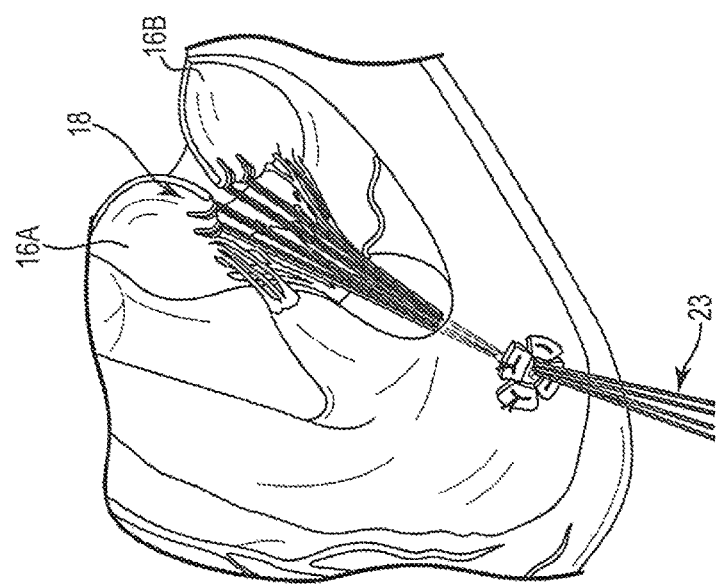
Figure 10D:
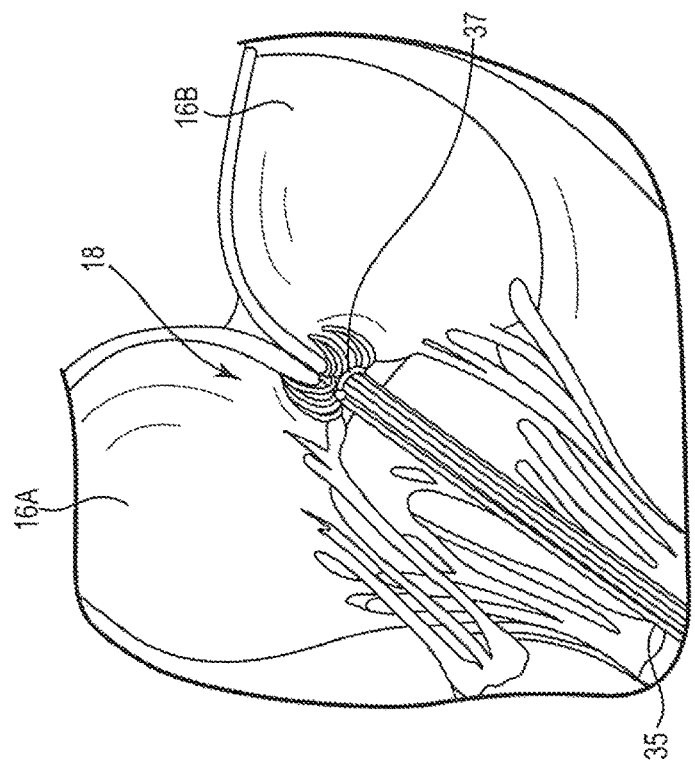
Figure 10C:
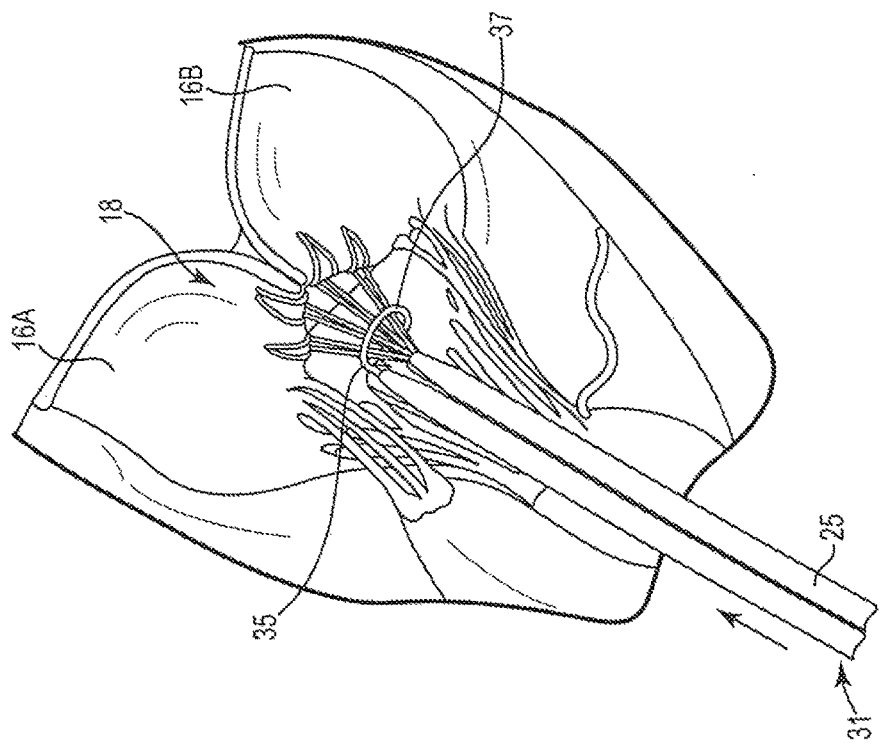
Figure 11:
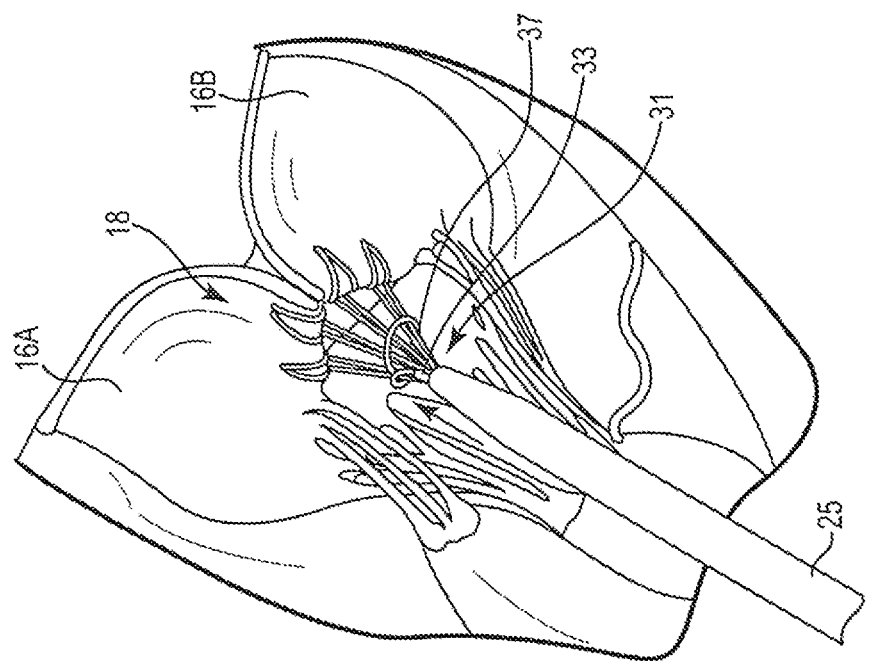
FIG. 11 schematically depicts a portion of a method of performing an edge to edge repair of a heart valve with sutures on a beating heart of a patient according to an embodiment of the present invention.

Referring now to FIGS. 10A-10D, a method of performing an edge to edge repair of a heart valve with sutures on a beating heart of a patient according to another embodiment of the present invention is schematically depicted. The method depicted in FIGS. 10A-10D is similar in most respects to the method described above with respect to FIGS. 9A-9I. A plurality of sutures depicted as, for example, four sutures 18 are inserted into the leaflets 16A, 16B as discussed above. In this embodiment, a single tourniquet tube 25 is advanced along all four suture pairs 23 as shown in FIG. 10B. In various embodiments, tourniquet tube 25 can define a single lumen through which all suture pairs extend or can define an individual lumen within the tube for each suture pair. The procedure proceeds as described above with the loop 37 of a suture 35 of a ligature assembly 31 used to secure the sutures 18 and leaflets 16A, 16B under tension. Use of a single tourniquet tube 25 can simplify and speed up the procedure with respect to using individual tourniquet tubes 25A-25D for each suture pair 23A-23D as described above. FIG. 11 depicts a further alternative in which the entire ligature assembly 31, including the plastic tube 33 and the ligature loop 37 are advanced to the leaflets 16A-16B to secure the sutures 18 from inside of the tourniquet tube 25 rather than from the outside as previously described. Such an embodiment can provide the advantage of further protection against interference with subvalvular and other internal heart structures such as chordae tendonae due to the loop being inside the tourniquet tube and thereby precluded from contacting such structures. In a further embodiment, rather than advancing a separate ligature assembly through the inside of the tourniquet, the suture loop can be incorporated into the tourniquet itself. In one such embodiment, the inner wall of the tourniquet tube can include a channel that includes the suture loop. Once the tourniquet is in place over the sutures and against the leaflets, the suture loop can be tightened from a proximal end of the tourniquet so that it is released from a distal end of the tourniquet and secured around the sutures.

As noted above, one benefit of utilizing tourniquet tubes as described herein is to minimize interference with internal structure of the heart. To this end, tourniquet tubes are preferably provided with a minimal external form factor while still providing an opening into which sutures can be easily inserted. Individual tourniquet tubes 25A-25D can, for example, each have an outer diameter between about 2 mm to about 10 mm and an inner lumen having a diameter between about 1 mm to about 8 mm. A single tourniquet tube 25 utilized for all suture pairs can, for example, have an outer diameter between about 2 mm and about 10 mm and an inner lumen having a diameter between about 1 mm and about 8 mm. The length of any given tourniquet tube can, for example, be between about 10 mm and about 15 mm.

Figure 13A:
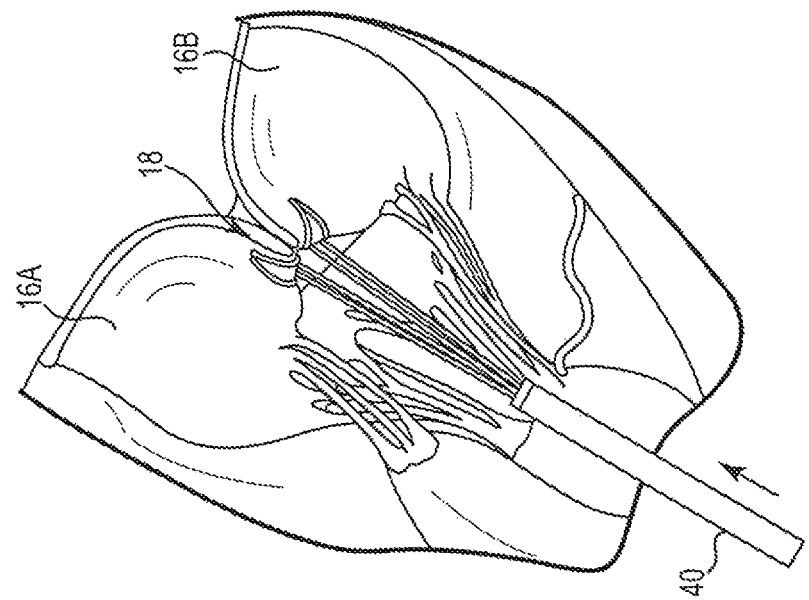
Figure 13B:
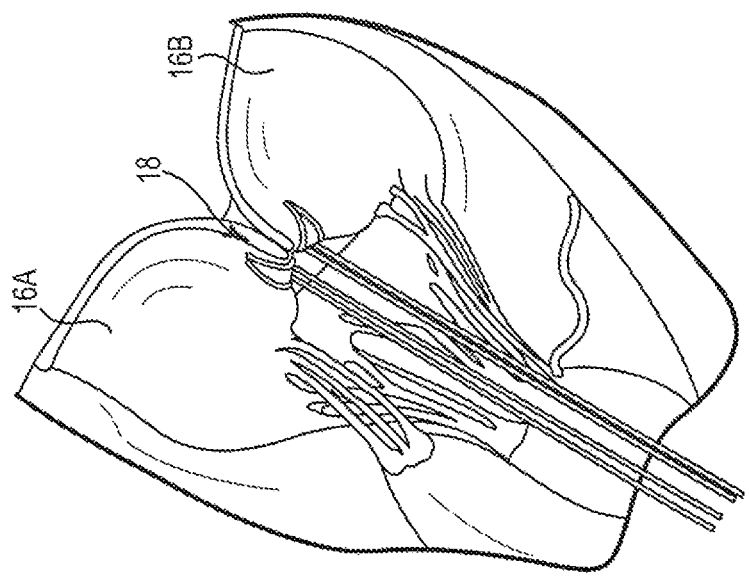

In a further embodiment depicted in FIGS. 13A-13D, the functions of the tourniquet tube(s) and ligature assembly described above can be incorporated into a single stabilizing tourniquet 40. After a plurality of sutures 18 are inserted into leaflets 16A, 16B as described above and depicted in FIG. 13A, the stabilizing tourniquet 40 can be advanced over the sutures. Also, as described above, after the stabilizing tourniquet 40 has been advanced to the leaflets the efficacy of the procedure can be assessed. In one embodiment, the stabilizing tourniquet 40 includes a detachable clip 42 at a distal end of the tourniquet. Once the positioning of the sutures 18 is determined to be effective, the clip 42 can be deployed from a body portion 44 of the stabilizing tourniquet 40 and cinched around the sutures 18. In one embodiment, clip 42 can be deployed by rotating body portion 44 in a first direction as depicted in FIG. 13C to tighten the clip 42 around the sutures 18 to hold the sutures 18 in the desired position. The body portion 44 can then be rotated in the opposite direction to detach the body portion 44 from the clip 42 and the body portion 44 withdrawn as shown in FIG. 13D. The clip 42 then remains in place holding the sutures and leaflets in the desired position and the procedure is concluded as described herein. In various embodiments, the clip 42 may be comprised of a same or similar plastic material as the stabilizing tourniquet or may be a different material (e.g., metal). In a further embodiment, rather than a clip 42 a suture loop may be encapsulated at the distal end of the stabilizing tourniquet such that pulling on a proximal end of the suture causes the suture to detach from the tourniquet and tighten around the sutures.

Figure 12:
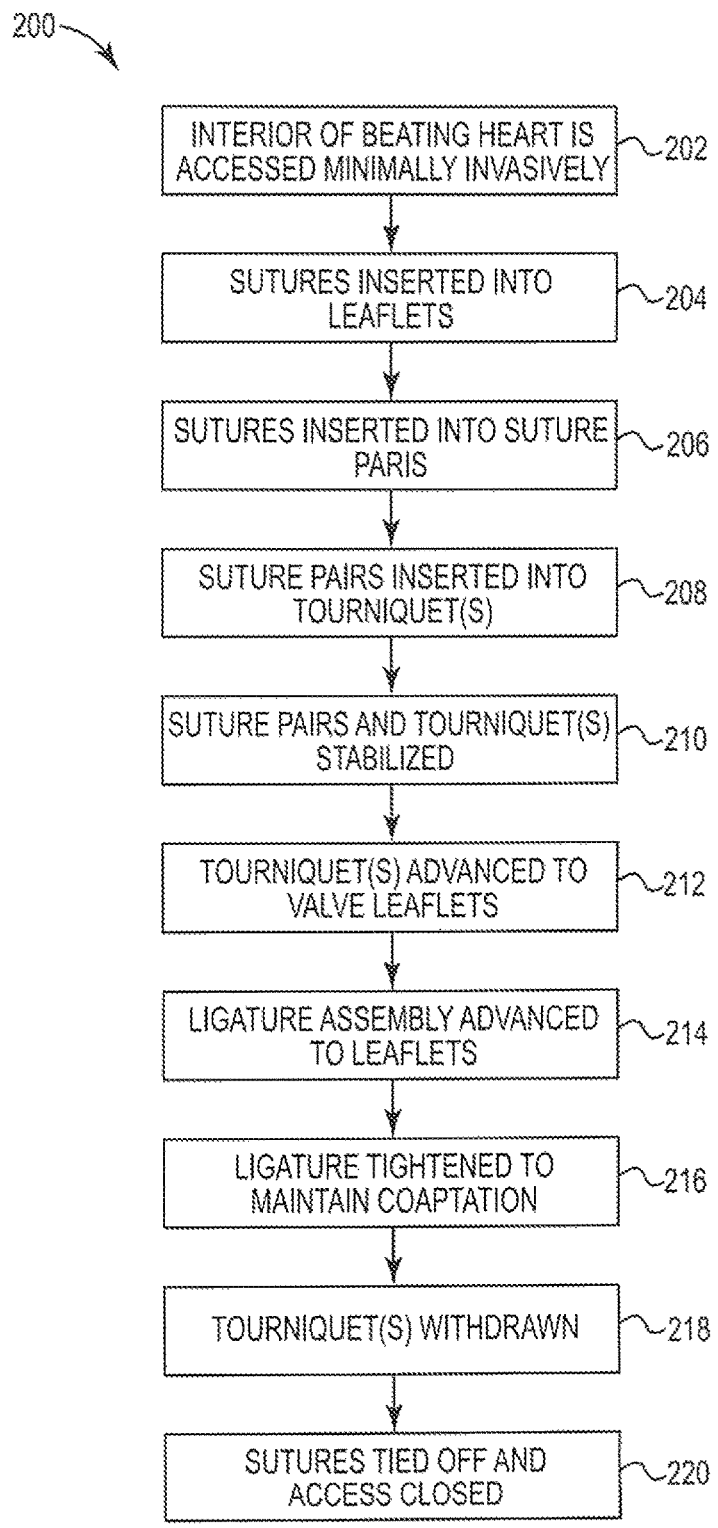
FIG. 12 is a flowchart depicting method steps or a method of performing an edge to edge repair of a heart valve with sutures on a beating heart of a patient according to embodiments of the present invention.

FIG. 12 depicts a flowchart of method steps for methods 200 for performing an edge to edge repair of a heart valve with sutures on a beating heart of a patient according to embodiments of the present invention. At step 202, the interior of the heart is initially accessed according to any procedure known in the art. In some embodiments, the heart is accessed via an incision in the apical region of the heart, such as through the apex of the left ventricle. In other embodiments, the heart can be accessed endovascularly, such as through the femoral vein. At step 204, one or more sutures is inserted into each of a plurality of heart valve leaflets of a heart valve, such as the mitral valve, within the heart with a suturing device such as the device described with respect to FIGS. 4-8F. In various embodiments, the device can be withdrawn after inserting each suture, reloaded with another suture and inserted into the heart to insert each subsequent suture or can be reloaded with additional sutures for insertion without being withdrawn from the heart.

The sutures are then divided into suture pairs at step 206, with each suture pair consisting of one suture end extending from a suture inserted through a first valve leaflet, such as the anterior leaflet of the mitral valve, and one suture end extending from a suture inserted through a second valve leaflet, such as the posterior leaflet of the mitral valve. One or more small tourniquet tubes can then be inserted over the sutures pairs at step 208. As described above, in various embodiments each suture pair can be provided with an individual tourniquet tube or a single tourniquet tube can be utilized for all suture pairs. A stabilizing device such as a mosquito forceps can optionally be used at step 210 to stabilize the tourniquet tube(s) on the suture pairs prior to advancing the tourniquet tube(s) along the suture pairs up to the leaflets at step 212 to draw the sutures together to coapt the leaflets. The tourniquet tube(s) and sutures can then be secured with the forceps clamping the tourniquet tube(s) and sutures in relative position to each other. Proper valve function can be confirmed using real-time transesophageal echocardiography. A ligature assembly is then advanced to the leaflets at step 214 and its suture loop tightened around the sutures to secure the sutures at the appropriate tension to maintain the leaflets in an edge to edge, coapted configuration at step 216.

As described above, in various embodiments the ligature assembly can be advanced from around the one or more tourniquet tube(s) or within a single tourniquet tube. As also described above, in various embodiments a single stabilizing tourniquet having an attached clip or suture loop can be employed in place of separate tourniquet tube(s) and ligature assembly. After the ligature suture loop (or clip) has been secured, the tourniquet tube(s) can then be withdrawn at step 218. The sutures through the leaflets and/or ligature suture are then tied off and the access point to the heart closed at step 220. The valve leaflets will therefore remain in a coapted, edge to edge position maintained by the tensioned sutures, preventing leaflet prolapse and valve regurgitation.

EXAMPLE

Transapical edge to edge mitral valve repair consistent with the above-described embodiments was performed and proven safe and efficacious in a patient with isolated P2 scallop flail/prolapse. The repair was performed to treat bileaflet commissural prolapse as a solution for a patient not considered appropriate for any other approved transcatheter repair. The patient was 72 years old and had previously had multiple left thoracotomies to treat recurrent pneumothorax presented with progressive dyspnea and New York Heart Association (NYHA) Functional Class III. Echocardiography demonstrated severe paracommissural mitral valve regurgitation. Multi-slice computed tomography demonstrated a severe calcification of the A1, P1, and P2 annular segments of the valve.

The procedure was performed under general anesthesia with standard postero-lateral ventricular access, using guidance from transesophageal echocardiography (2-D and 3-D TEE). Three sutures were implanted on the posterior leaflet (P2-P3) and three on the anterior leaflet (A2-A3). After implantation, coaptation of the two leaflets was achieved by putting tension on all of the sutures together with a tourniquet tube. Once stable coaptation was achieved, all sutures were tightened at the base of the ventricular edge of the leaflets using a ligature loop assembly (Surgitie Loop by Covidien) that was advanced over the tourniquet under echo guidance. Once the loop was secured, the tourniquet was removed, the ventricular purse string access was closed, and the sutures through the leaflets and the end of the ligature suture were fixed on the epicardium surface. The patient was discharged and at a one month follow up was asymptomatic (NYHA Functional Class I) with mild to moderate MR, confirmed by echocardiograhpic and multi-slice computed tomography.

Although specifically described with respect to the mitral valve, it should be understood the devices described herein could be used to treat any other malfunctioning valve, such as the tricuspid and aortic valves. Further, although not specifically described herein, it should be understood that the devices described in the present application could be implanted into the beating heart of the patient via various access approaches known in the art, including transapical approaches (e.g., through the apex of the left ventricle) and transvascular approaches, such as transfemorally (through the femoral vein). One example of a transapical access approach that could be employed is described in U.S. Pat. No. 9,044,221, previously incorporated by reference herein. One example of a transvascular access approach that could be employed is described in U.S. Patent Publication No. 2013/0035757, previously incorporated by reference herein. This versatility in access approach enables the access site for the procedure to be tailored to the needs of the patient.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A method of minimally invasively performing an edge to edge heart valve leaflet repair on a beating heart of a patient, comprising:
    accessing an interior of a beating heart of a patient minimally invasively;
    inserting one or more sutures into each of a first valve leaflet and a second valve leaflet of a heart valve in the beating heart of the patient, each suture having a pair of suture ends;
    providing a plurality of suture pairs, each suture pair including one of the pair of suture ends of a suture inserted through the first valve leaflet and one of the pair of suture ends of a suture inserted through the second valve leaflet;
    advancing one or more tourniquet tubes over the suture pairs towards the heart valve such that the sutures are drawn into a coaptation tension in which the first valve leaflet and the second valve leaflet are in a coapted position;
    securing the sutures at the coaptation tension;
    withdrawing the one or more tourniquet tubes from the suture ends after securing the sutures; and
    anchoring the suture ends at a wall of the heart with the sutures in the coaptation tension,
    wherein securing the sutures at the coaptation tension includes:
        securing the one or more tourniquet tubes with respect to the suture pairs with the sutures in the coaptation tension;
        advancing a suture loop of a ligature suture along the one or more tourniquet tubes to the first valve leaflet and the second valve leaflet; and
        securing the suture loop around the sutures with the sutures in the coaptation tension.

2. The method of claim 1, wherein advancing the suture loop along the one or more tourniquet tubes advances the suture loop along an exterior of the one or more tourniquet tubes.

3. The method of claim 1, where advancing the suture loop along the one or more tourniquet tubes advances the suture loop along an interior of a single tourniquet tube.

4. The method of claim 1, where the one or more tourniquet tubes includes a separate tourniquet tube for each suture pair.

5. The method of claim 1, wherein the one or more tourniquet tubes is a single tourniquet tube advanced over all suture pairs.

6. The method of claim 1, further comprising assessing valve functioning prior to securing the sutures at the coaptation tension.

7. The method of claim 1, wherein anchoring the suture ends at a wall of the heart anchors the suture ends in an apical region of the heart.

8. The method of claim 1, wherein accessing an interior of a beating heart of a patient minimally invasively access the interior of the beating heart through an apical region of the heart.

9. A method of minimally invasively performing an edge to edge heart valve leaflet repair on a beating heart of a patient, comprising:
    accessing an interior of a beating heart of a patient minimally invasively;

inserting one or more sutures into each of a first valve leaflet and a second valve leaflet of a heart valve in the beating heart of the patient, each suture having a pair of suture ends;

providing a plurality of suture pairs, each suture pair including one of the pair of suture ends of a suture inserted through the first valve leaflet and one of the pair of suture ends of a suture inserted through the second valve leaflet;

advancing one or more tourniquet tubes over the suture pairs towards the heart valve such that the sutures are drawn into a coaptation tension in which the first valve leaflet and the second valve leaflet are in a coapted position;

securing the sutures at the coaptation tension;

withdrawing the one or more tourniquet tubes from the suture ends after securing the sutures; and anchoring the suture ends at a wall of the heart with the sutures in the coaptation tension, and wherein the one or more tourniquet tubes is a single tourniquet tube having a clip at a distal end of the single tourniquet tube and wherein securing the sutures at the coaptation tension includes securing the sutures at the coaptation tension with the clip and disconnecting a body portion of the single tourniquet tube from the clip.

10. The method of claim 9, wherein securing the sutures at the coaptation tension with the clip includes rotating the body portion of the single tourniquet tube in a first direction and disconnecting the body portion from the clip includes rotating the body portion in a second direction opposite of the first direction.

* * * * *